United States Patent [19]

Itatani et al.

[11] 3,940,426
[45] Feb. 24, 1976

[54] PROCESS FOR PRODUCING BIPHENYLTETRACARBOXYLIC DIANHYDRIDES

[75] Inventors: Hiroshi Itatani; Mikito Kashima; Masaoki Matsuda; Hataaki Yoshimoto; Hiroyuki Yamamoto, all of Ichihara, Japan

[73] Assignee: UBE Industries, Ltd., Ube, Japan

[22] Filed: Jan. 16, 1973

[21] Appl. No.: 324,050

[30] Foreign Application Priority Data
Apr. 3, 1972 Japan............................. 47-32554
May 19, 1972 Japan............................ 47-49143

[52] U.S. Cl....... 260/346.3; 260/515 P; 260/524 R; 260/524 N
[51] Int. Cl.². ........................................ C07D 307/89
[58] Field of Search............. 260/346.3, 346.4, 524, 260/525

[56] References Cited
UNITED STATES PATENTS

| | | | |
|---|---|---|---|
| 3,173,947 | 3/1965 | Essen et al.......................... | 260/524 |
| 3,179,614 | 4/1965 | Edwards............................. | 260/30.2 |
| 3,338,923 | 8/1967 | Peterlein et al.................... | 260/346.3 |
| R27,296 | 2/1972 | Ichikawa et al................... | 260/524 R |

OTHER PUBLICATIONS

Ichikawa et al., C. A., Vol. 74, 126336k.
Groggins, "Unit Processes Inorganic Synthesis," 4 edition, 1952, p. 658.

Primary Examiner—Harry I. Moatz
Attorney, Agent, or Firm—Sughrue, Rothwell, Mion, Zinn & Macpeak

[57] ABSTRACT

A process for separating and purifying biphenyltetracarboxylic dianhdride isomers from a mixture of these isomers by fractional crystallization in aliphatic acid anhydrides or acetone. The isomeric mixture is obtained by heating biphenyltetracarboxylic acids, optionally in the presence of an aliphatic acid anhydride. The biphenyltetracarboxylic acids are obtained by oxidizing coupling dimers of o-xylene or by hydrolyzing coupling dimers of dimethyl phthalate.

3 Claims, 5 Drawing Figures

PROCESS FOR PRODUCING BIPHENYLTETRACARBOXYLIC DIANHYDRIDES

BACKGROUND OF THE INVENTION

1. Field Of The Invention

This invention relates to biphenyltetracarboxylic dianhydrides and a process for their production.

2. Description Of The Prior Art

It has been known that 2,3,2',3',- and 3,4,3',4'-biphenyltetracarboxylic dianhydrides are useful, for example, as starting material for producing of polyimides. See, e.g., U.S. Pats. Nos. 3,179,614 and 3,179,630 to 3,179,633.

However, no method is yet known which is commercially acceptable for the mass-production of these dianhydrides.

Previously (Japanese Patent Applications 46-87579, 46-91136, 47-32554, 47-49143) we studied a method of producing biphenyltetracarboxylic dianhydrides on an industrial scale. As a result, we found that when dimethyl ortho-phthalate or ortho-xylene is reacted in the presence of an organic palladium salt and a certain additive under oxygen pressure, a dimerized product thereof (a mixture of three isomers), which is an oxidative coupling reaction product, can be produced at high yield, the this dimer can be easily converted to an isomeric mixture of biphenyltetracarboxylic acids by a procedure such as hydrolysis or oxidation, and that when the resulting mixture is heated biphenyltetracarboxylic dianhydrides can be produced commercially.

However, the isomeric mixture of biphenyltetracarboxylic dianhydrides so obtained contains 2,3,3',4'-(10~80%) and 3,4,3',4'-(90~17%) isomers as the main products and unreacted biphenyltetracarboxylic acid isomers as impurities. This isomeric mixture is extremely difficult to separate and purify at good yields, even by recrystallization or distillation. Although the mixture also contains a 2,3,2',3'-isomer (0~3%), since the amount of this isomer is very small at the time of producing the dimerized product, it is also present in only small amounts (0~3%) in the isomeric mixture of biphenyltetracarboxylic dianhydrides.

This led us to an extensive study on methods of separating the desired isomers, especially the 2,3,3',4'- and 3,4,3',4'-isomers, in pure form from the isomeric mixture of biphenyltetracarboxylic dianhydrides. Consequently, we found that diphenyltetracarboxylic dianhydrides vary greatly in their solubility in aliphatic acid anhydrides or ketones according to the type of isomer, and the isomers can be easily separated according to this difference in solubility. We further found that when the isomers are recrystallized from the aliphatic acid anhydrides, the unreacted biphenyltetracarboxylic acids present in the isomers can be converted to biphenyltetracarboxylic dianhydrides and small amounts of other impurities can be separated and removed, whereby the desired isomers of biphenyltetracarboxylic dianhydride can be obtained in pure form.

As previously stated (Japanese Patent Application 46-87579), we found that when dimethyl ortho-phthalate is reacted in the presence of an organic palladium salt and a certain additive under oxygen pressure, tetramethyl biphenyltetracarboxylate, its dimer, is produced at high yield by oxidative coupling. This tetramethyl biphenyltetracarboxylate comprises 2,3,2',3'-, 2,3,3',4'- and 3,4,3',4'-isomers. Although differing somewhat according to the conditions of producing the tetramethyl biphenyltetracarboxylates, the proportions of the isomers are about 0~3% for the 2,3,2',3'-isomer, about 54–80% for the 2,3,3',4'-isomer, and about 43~17% for the 3,4,3',4'-isomer. Since the amount of the 2,3,2',3'-isomer is extremely small, it can be separated to some extent by distillation, and can be ignored for many practical purposes. However, we found that it is very difficult to economically separate and purify the 2,3,3',4'- and 3,4,3',4'-isomers.

These isomers are insoluble in water and they cannot be separated by mere recrystallization from an organic solvent such as methanol, ethanol, tetrahydrofuran, methyl acetate, carbon tetrachloride or methyl cellosolve. Furthermore, because of their high boiling point, it is not practical to separate and purify them by distillation. When the isomeric mixture is subjected to fractional crystallization using an organic solvent such as methanol, butanol, ether, tetrahydrofuran, toluene, methyl cellosolve, nitrobenzene, chloroform, carbon tetrachloride, acetone, methyl acetate or ethanol-ether, if the ratio of the 2,3,3',4'- and 3,4,3',4'-tetramethyl biphenyltetracarboxylates is at least 1:2, the constituent which is present in excess is first precipitated, but both isomers in a ratio of about 1:1 still remain in the solution. They cannot be separated economically and quantitatively.

SUMMARY OF THE INVENTION

We have conducted extensive studies on methods of separating, in pure form, the isomers from an isomeric mixture of tetraalkyl biphenyltetracarboxylates. As a result, we discovered that when such an isomeric mixture is hydrolyzed to an isomeric mixture of biphenyltetracarboxylic acids, these isomers can be easily separated in water or an aqueous solvent since 2,3,2',3'-, 2,3,3',4'- and 3,4,3',4'-biphenyltetracarboxylic acids all differ greatly in water solubility. According to the present invention, there can be provided biphenyltetracarboxylic acid isomers by oxidizing tetramethyl biphenyls formed by the oxidative coupling of o-xylene in the presence of an organic acid salt of palladium.

Similarly, there can be provided biphenyltetracarboxylic acid isomers by hydrolyzing biphenyltetracarboxylates formed by the oxidative coupling of dimethyl phthalate in the presence of an organic acid salt of palladium.

The isomeric mixture of biphenyltetracarboxylic acids so obtained contains 2,3,2',3'-(0–3%), 2,3,3',4'-(10–80%) and 3,4,3',4'-(90–17%) isomers. Since the amount of a 2,3,2',3'-isomer is extremely small, the 2,3,2',3'-isomer can easily be separated from the other isomers by distillation or recrystallization.

Furthermore, there is provided a process for separating and purifying biphenyltetracarboxylic anhydride isomers from a mixture of 2,3,3',4'- and 3,4,3',4'-isomers by fractional crystallization of the acid anhydrides thereof obtained by heating a mixture thereof in the presence of an aliphatic acid anhydride or a ketone.

On the other hand, acid anhydrides of biphenyltetracarboxylic acids obtained by heating under reflux with an aliphatic acid anhydride can be separated and purified from a mixture by fractional crystallization.

By following the teachings of the present invention, 2,3,3',4'-biphenyltetracarboxylic dianhydride, a novel substance can be produced.

It is an object of this invention to provide a process for producing biphenyltetracarboxylic dianhydride isomers from an isomeric mixture of biphenyltetracarboxylic acids.

Another object of this invention is to provide a process which comprises producing an isomeric mixture of biphenyltetracarboxylic dianhydrides from an isomeric mixture of biphenyltetracarboxylic acids, and separating this mixture into the constituent dianhydride isomers.

Still another object of this invention is to provide a process for separating an isomeric mixture of biphenyltetracarboxylic acids into the constituent isomers and a process for producing biphenyltetracarboxylic dianhydrides from these isomers.

DETAILED DESCRIPTION OF THE INVENTION

According to one aspect of this invention, there is provided a process for separating and purifying an isomeric mixture of biphenyltetracarboxylic dianhydrides which comprises separating said mixture into the constituent isomers in the presence of an aliphatic acid anhydride or ketone or mixture thereof in an amount of 1 – 500 times by weight, preferably 2 – 10 times by weight, the weight of the isomers.

Separation of the biphenyltetracarboxylic dianhydrides will usually be performed in the presence of the recited aliphatic acid anhydride(s) and for ketone(s) by heating at a temperature of from about 50°C to about 250°C and at a pressure of from about 1 atm to about 30 atm. Preferred separation/purification conditions are from 100°C to 150°C and atmospheric pressure. Heating will be terminated when the desired separation is achieved, generally in a period of time of from about 2 hours to about 20 hours, more typically 4 to 8 hours.

It has been experimentally confirmed that the 2,3,3',-4'-biphenyltetracarboxylic dianhydride is more soluble in an aliphatic acid anhydride or ketone than the 3,4,3',4'-isomer.

Figure 1:
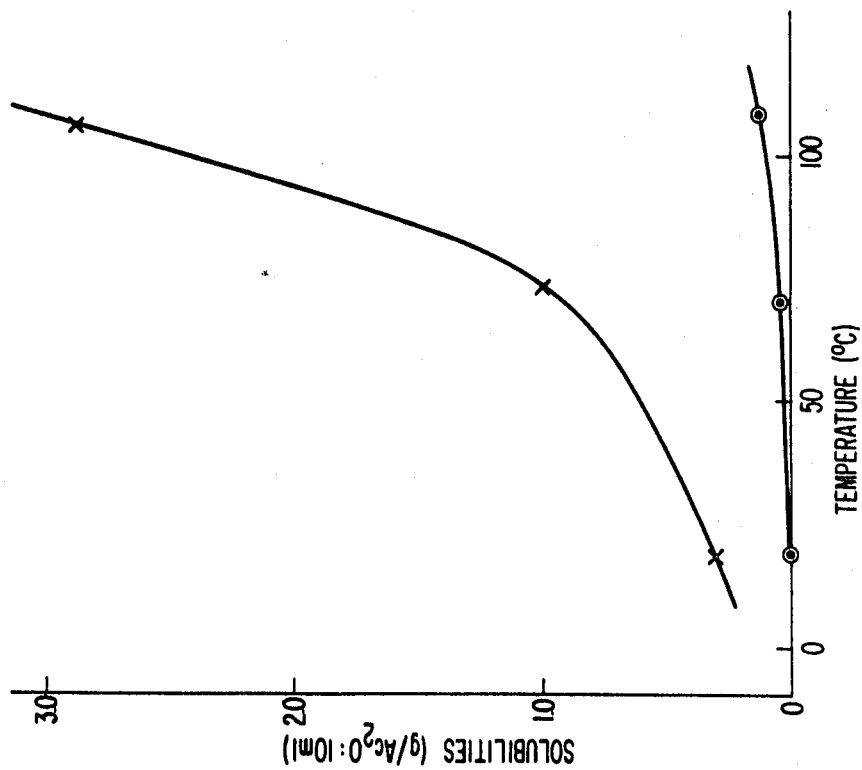
FIG. 1 is a graphic representation showing the solubilities of 2,3,3',4'-biphenyltetracarboxylic dianhydride and 3,4,3',4'-biphenyltetracarboxylic dianhydride in acetic anhydride plotted against varying temperatures, the symbol $x$ showing the solubility of the 2,3,3',4'-isomer and the symbol showing that of the 3,4,3',4'-isomer.

Referring to FIG. 1, the ordinate represents the solubility (g/acetic anhydride: 10 ml.) and the abscissa the temperature in °C. The measurement of the solubility was performed by maintaining separate mixtures of 2.5 g of the 2,3,3',4'-isomer and 5 ml. of acetic anhydride and a mixture of 1 g of the 3,4,3',4'-isomer and 20 ml. of acetic anhydride at a predetermined temperature to dissolve each of the isomers in the acetic anhydride, separating the insoluble matter by filtration, drying the filtrate and weighing it, to thereby obtain the amount of the isomer dissolved in acetic acid at the specified temperature.

According to another aspect of this invention, there is provided a process for producing biphenyltetracarboxylic dianhydrides, which comprises hydrolyzing an isomeric mixture of tetraalkyl esters of biphenyltetracarboxylates such as tetramethyl, tetraethyl or tetrabutyl-esters, separating the resulting isomeric mixture of biphenyltetracarboxylic acids into the constituent isomers in water or an aqueous solvent, and then heating the biphenyltetracarboxylic acid isomers to convert them to the corresponding dianhydrides.

Figure 2:
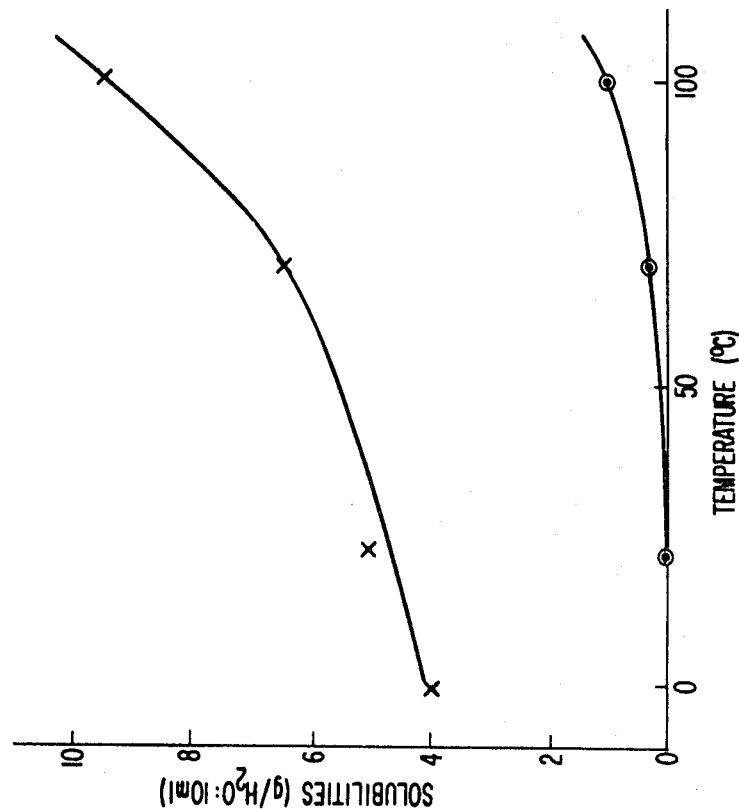
FIG. 2 is a graphic representation showing the solubilities of 2,3,3',4'- and 3,4,3',4'-biphenyltetracarboxylic acid in water plotted against varying temperatures, the symbol $x$ showing the solubility of the 2,3,3',-4'-isomer and the symbol showing that of the 3,4,3',-4'-isomer.

Of the biphenyltetracarboxylic acid isomers, the 2,3,2',3'-isomer has the largest solubility in water or in an aqueous solvent, followed by the 2,3,3',4'-isomer and the 3,4,3',4'-isomer in order of decreasing solubility. The solubilities of these latter-mentioned biphenyltetracarboxylic acid isomers in water are shown in FIG. 2. The solubility was measured by maintaining each of a mixture of 9.35 g of 2,3,3',4'-biphenyltetracarboxylic acid and 10 ml. of water and a mixture of 7.53 g of 3,4,3',4'-biphenyltetracarboxylic acid and 20 ml. of water at a predetermined temperature to dissolve each of the isomers in water, separating the insoluble matter by filtration, drying the filtrate, and weighing it, to thereby obtained the amount of each isomer dissolved at the specified temperature. The ordinate in FIG. 2 shows the solubility (g/$H_2O$: 10 ml.) and the abscissa the temperature in °C. The symbol $x$ shows the solubility of the 2,3,3',4'-biphenyltetracarboxylic acid at the respective temperatures, and the symbol that of the 3,4,3',4'-biphenyltetracarboxylic acid at the respective temperatures.

Figure 3:
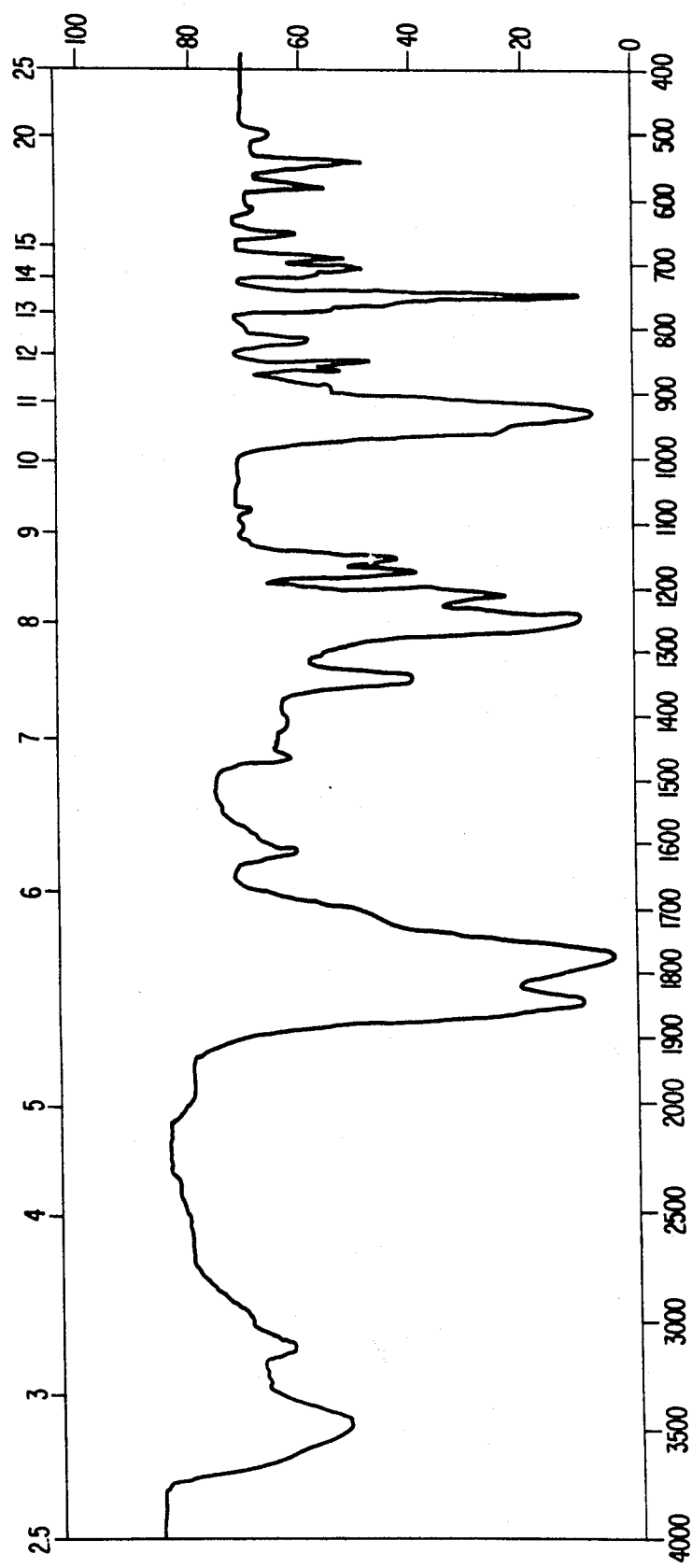
FIG. 3 is the infrared absorption spectrum of 2,3,3',-4'-biphenyltetracarboxylic dianhydride.

2,3,3',4'-biphenyltetracarboxylic dianhydride is a novel substance. Polyimides can be produced therefrom under the same conditions as are disclosed in U.S. Pat. No. 3,179,614, which polyimides illustrate excellent heat resistance. It can easily be produced by heating 2,3,3'-4'-biphenyltetracarboxylic acid at 200°–350°C. or by refluxing in the presence of an aliphatic acid anhydride. The reaction is conducted in the molten state under reduced pressure, e.g., below 760 mm Hg to 1 mm Hg for about 10 minutes to about 10 hours. The reaction time varies with molecular weight to be used. In the pressure of an aliphatic acid anhydride, the reaction is conducted by reflux heating in the presence of about 2 to 10 times by weight of the anhydride to ester for about 2 to 20 hours. It can be purified and isolated in accordance with the present invention. The infrared absorption spectrum of the 2,3,3',4'-biphenyltetracarboxylic dianhydride is shown in FIG. 3. The stretching vibration of the carbonyl group shows itself as two peaks in the vicinity of 1800 $cm^{-1}$. The 2,3,3',4'-biphenyltetracarboxylic dianhydride is in the form of white crystals having a melting point of 197° to 200°C. An elemental analysis thereof is as follows: for $C_{16}H_6O_6$ calculated C=65.31, H=2.07; found C=65.08, H=2.07.

Examples of the aliphatic acid anhydride use in the present invention are acetic anhydride, propionic anhydride butyric anhydride, caproic anhydride, valeric acid anhydride, heptanoic acid anhydride, caproic acid anhydride etc. It is preferred that the acid anhydride or the ketone used in this invention have a boiling point below 250°C since the acid anhydride (or the corresponding free acid derived from the acid anhydride) or the ketone can easily be removed from the reaction system by distillation after the reaction has been completed. Preferred anhydrides are the $C_2$ to $C_5$ aliphatic acid anhydrides. Of these, acetic anhydride is most preferred. When a ketone is used, it is desirable to remove as much water as possible from it, i.e., a substantially anhydrous ketone is preferably used, such as acetone, diethylketone, diisopropylketone and dibutylketone.

The present invention makes it possible to easily separate and purify 2,3,3',4'-isomer (10–80%) and 3,4,3',4'-isomer (90–17%) from an isomeric mixture containing these biphenyltetracarboxylic dianhydride isomers. In the presence of the aliphatic acid anhydride, the 3,4,3',4'-isomer is first precipitated as crystals, and then by concentrating the filtrate, e.g., by distillation, the 2,3,3',4'-isomer is precipitated as crystals. As explained at a later point, the 2,3,2',3'-isomer is usually either present at very low proportions (0–3%) or removed by a prior distillation or recrystallization. Hence, for a commercial process, it may be ignored in many instances.

The hydrolysis of an isomeric mixture of tetramethyl biphenyl tetracarboxylates to form biphenyltetracarboxylic acids may be performed by any method. However, since tetramethyl biphenyl tetracarboxylates are insoluble in water, it is not preferred to perform the hydrolysis in an aqueous solution containing only an alkali salt such as sodium hydroxide, potassium hydroxide or sodium carbonate, or, on the other hand, merely containing a mineral acid such as sulfuric acid, hydrochloric acid or nitric acid, though such systems may be used.

It is also possible to heat the isomeric mixture together with an alkali salt and a water-miscible organic solvent such as an alcohol, e.g., methanol, acetone or dioxane, and neutralize and acidify (below pH 1) the resulting alkali salts of biphenyltetracarboxylic acids with a mineral acid to precipitate the biphenyltetracarboxylic acids. However, in order to increase the solubility of the mixture in water, the alkali salt must be used in large excess (larger than 4 molar amounts of ester), and therefore this method is not highly preferred because of the need for large quantities of the alkali salt and the mineral acid, which is also used in amount more than 4 molar times the amount of ester. The above method, however, may safely be employed to accomplish the hydrolysis with a strong acid.

Our work shows that the hydrolysis of tetramethyl biphennyltetracarboxylates is most effectively carried out by heating them in the presence of an organic solvent which is miscible with water and dissolves the tetramethyl biphenyltetracarboxylates, such as acetic acid, propionic acid, methanol, ethanol, acetone, dioxane, propyl alcohol or glycolic acid and a small amount of a mineral acid such as sulfuric acid, hydrochloric acid, nitric acid or phosphoric acid. It is especially preferred to perform the hydrolysis using a mineral acid (1~1/100 parts)-water (1~10 parts)-acetic (1~10 parts) acid system, all parts being by weight based on 1 part by weight of ester. Since acetic acid dissolves the ester, the contact of an ester with strong acid increases. Acetic acid further accelerates hydrolysis differently from other organic solvents, since acetic acid dissociates. According to this method of hydrolysis, the amount of the mineral acid can be reduced, and the use of the mineral acid ($HCl$, $H_2SO_4$, $HBr$, $HNO_3$) in an amount of 1 to 1/100 parts by weight based on the isomeric mixture of tetramethyl biphenyltetracarboxylates easily permits the accomplishment of hydrolysis.

For example, the following hydrolysis conditions have been found quite useful in practicing the present invention:

1. using alkalis as described above:
   NaOH or KOH; 0.5–1.5 weight parts (at least 4 moles per mole of ester),
   $H_2O$; 1–10 weight parts,
   water miscible organic solvent, e.g., methanol; 10 times the weight of NaOH or KOH (preferably; $H_2O$/methanol in a 1/4–1/1 weight ratio)
   reaction temp.; 50°–100°C
   reaction time; 2–10 hours
2. using acids as described above:
   98% $H_2SO_4$; 1/100 – 1 weight parts per weight part of ester, or
   35% HCl; 1/30 – 3 weight parts per weight part of ester,
   $H_2O$; 1 – 10 weight parts per weight part of ester,
   acetic acid; 1 – 10 weight parts per weight part of ester
   (preferably a HAc: $H_2O$ =1:1 weight mixture)
   reflux temp.; 50° – 100°C
   reaction time, 3–10 hr.

As indicated, system 2 is most preferred.

By such an hydrolysis, the isomeric mixture of tetramethyl biphenyltetracarboxylates is converted to an isomeric mixture of biphenyltetracarboxylic acids, which mixture is then separated into the constituent isomers in purified form.

The isomers may be successively separated by cooling the reaction product mixture obtained from the hydrolysis, separating the precipitated crystals of 3,4,3',4'-isomeric acid by filtration, and concentrating by distillation of the filtrate to precipitate crystals of 2,3,3',4'-isomeric acid.

Another method that can be used to separate the isomeric mixture into the constituent isomers comprises concentrating by distillation of the reaction product mixture to form a mixture of the crystals of the isomers, and then separating the mixture into the constituent isomer crystals in water or an aqueous solvent utilizing their difference in solubility. As the aqueous solvent, any compound that can dissolve the biphenyltetracarboxylic acid isomers, for example, a mixture of water and an organic solvent such as acetone, methanol, ethanol, acetic acid, Cellosolve, dimethylformamide, dioxane, tetrahydrofuran, etc., can be used.

During distillation to concentrate the reaction product mixture, materials such as water, acetone and tetrahydrofuran are removed from the system.

Usually the amount of water or aqueous solvent used (the aqueous solvent generally comprises at least about 20 weight % water, more preferably from 80 to 20 weight % water, balance organic solvent) is at least about 1 weight part per one weight part of isomers more preferably at least 2 weight parts per one weight part of isomers. Seldom will more than about 30 weight parts per one weight part of the isomer(s) be needed but one skilled in the art will appreciate these figures are merely exemplary and can be varied widely.

Separation will usually be conducted at a temperature of from about 0°C to about 50°C under atmospheric pressure. The biphenyltetracarboxylic acid isomers isolated may be further purified, if desired, by recrystallization from water, acetone, methanol, ethanol, etc.

When the biphenyltetracarboxylic acid isomeric mixture is placed in water or an aqueous solvent, crystals of 3,4,3',4'-biphenyltetracarboxylic acid are first precipitated. After separating these crystals, when the filtrate is concentrated by distillation, crystals of 2,3,3',4'-biphenyltetracarboxylic acid are precipitated, and by further concentration, crystals of a mixture of 2,3,2',3'- and 2,3,3',4'-isomer are precipitated. Since the amount of the 2,3,2',3'-isomer formed by the oxidative coupling of dimethyl ortho-phthalate is generally small (0~3%), almost all of this isomer is removed in a stage of obtaining tetramethyl biphenyltetracarboxylates by distillation, e.g., at 250° to 300°C/1 mmHg, of the reaction product, and the isomeric mixture of tetramethyl biphenyltetracarboxylates consists mainly of 2,3,3',4'- and 3,4,3',4'-isomers. It is not usually necessary therefore to separate the 2,3,2',3'-biphenyltetracarboxylic acid isomer.

In accordance with this invention, biphenyltetracarboxylic acid dianhydrides may be prepared merely by heating biphenyltetracarboxylic acids. However, by heating them in the presence of an aliphatic acid anhydride or an acid anhydride/ketone mixture in which the minimum molar % of anhydride is 20%, the isomers can be separated and continuously purified with great advantage. In this case, crystals of the isomers can be separated within the reaction product mixture, and the isomers can be separated and purified in situ.

When the biphenyltetracarboxylic acids are per se heated, heating is generally at a temperature of from about 200°C to about 350°C for about 10 min. to about 10 hours, with preferred conditions being in the ranges 200° to 300°C for 1 to 4 hours. The pressure of heating is not critical.

However, when the biphenyltetracarboxylic acids are heated in the presence of aliphatic acid anhydride(s) or aliphatic anhydride(s)/ketone(s), heating is generally at a temperature of from about 50°C to about 250°C and at a pressure of from about 1 atm to about 30 atms for about 2 hours to about 20 hours, with preferred conditions being 100° to 200°C, and 4 to 8 hours.

The aliphatic acid anhydride(s) or aliphatic anhydride(s)/ketone(s), and the proportions thereof, which are used are the same as those heretofore recited for the separation of the dianhydride isomers per se with the provise the minimum molar % of anhydride(s) in the anhydride(s)/ketone(s) mixture be 20%. It is preferred, when using such a mixture the anhydrides be present in an amount equal to the weight of the isomers.

The biphenyltetracarboxylic dianhydride isomers so separated can be further pruified by washing with, or recrystallizing from, an aliphatic acid anhydride or ketone.

The process for producing the biphenyltetracarboxylic dianhydride isomers according to this invention can be shown schematically as follows:

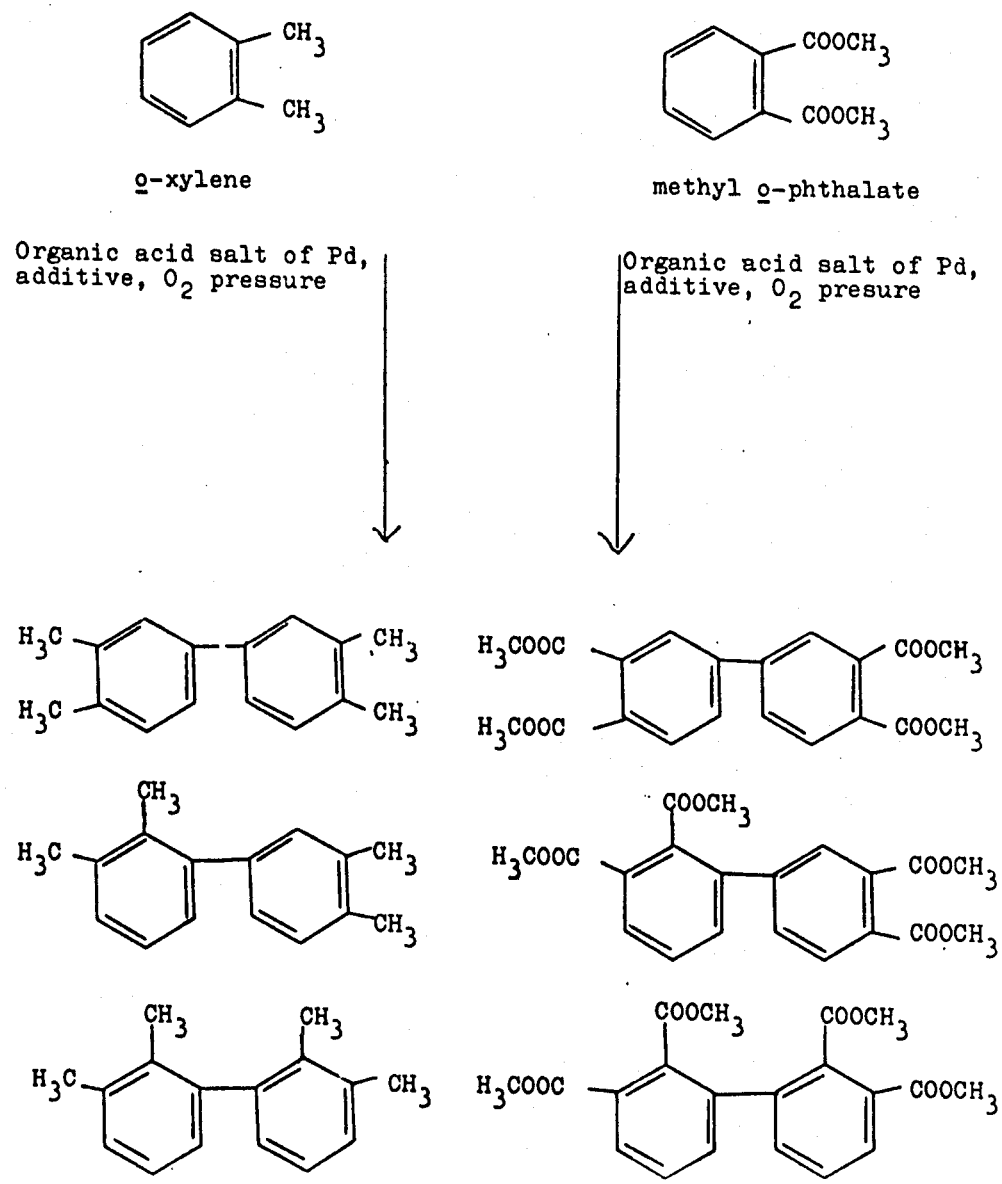

oxidation ↘ ↙ hydrolysis
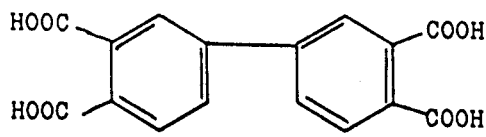
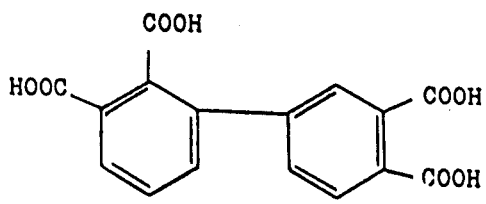
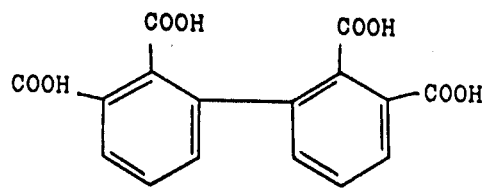
isomeric mixture
heating ↙ ↘ separating
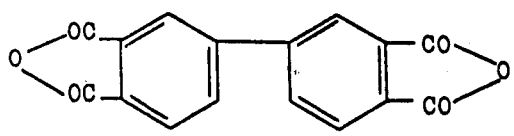
the constituent isomers
↓ dehydration
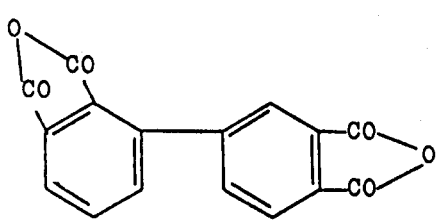
→ separation → isomers of dianhydrides

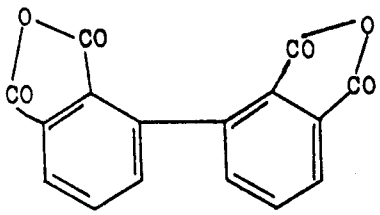

The production of a coupling dimer of o-xylene or dimethyl phthalate is performed by the oxidative coupling of o-xylene or dimethyl phthalate in the presence of an organic salt of palladium and an additive in an atmosphere of oxygen under pressure.

Examples of the organic acid salt of palladium that can be used in this invention are carboxylic acid salts such as palladium formate, palladium acetate, palladium propionate, palladium butyrate, palladium valerate or palladium oxalate, and aromatic carboxylates such as palladium terephthalate or palladium benzoate. There can also be used β-diketone compounds of palladium such as acetylacetonato palladium (II) or di-(trifluoroacetyl-acetonato) palladium (II), and also bis(dibenzalacetone) palladium (0). Of these, palladium acetate is preferred.

It is sufficient for reaction if the organic acid salt of palladium is present in an amount as small as $10^{-4}$ to $10^{-2}$ molar times, preferably $2 \times 10^{-4}$ to $2 \times 10^{-3}$, the amount of the moles of o-xylene or dimethyl phalate.

The use of the organic acid salt of palladium is essential in the present invention, and inorganic acid salts of palladium such as palladium chloride, a mixture of palladium chloride and sodium acetate, palladium sulfate and palladium nitrate are unsuitable.

It is important that the coupling reaction of dimethyl phthalate be performed in the presence of the organic acid salt of palladium and a certain specific additive in an atmosphere of oxygen under pressure. Examples of the additive are a chelating agent such as ethylenediaminetetraacetic acid or β-diketone compounds (acetylacetone, benzoylacetone, trifluoroacetylacetone, hexafluoroacetylacetone or benzoyltrifluoroacetone). The addition of such an additive markedly increases the yield of the coupling product. However, if other additives, such as sodium acetate, potassium acetate, lithium chloride, acetic acid, sulfuric acid, lithium nitrate, potassium nitrate, potassium sulfate or a polar solvent such as dimethyl formamide, acetonitrile or water, are present in the reaction system, they impede the progress of the reaction and cause a marked decrease in the amount of the coupled product yielded, sometimes prohibiting reaction.

When the coupling reaction is carried out in an autoclave made of stainless steel or iron, metal salts such as iron, nickel or chromium salts serve as contaminants to impede the reaction. But the addition of chelating agents such as ethylenediaminetetraacetic acid and β-diketones causes the reaction to proceed smoothly since the ethylenediaminetetraacetic acid forms a stable complex with such metals.

The amount of the β-diketone or ethylenediaminetetraacetic acid to be added is 0.5~5 molar times the amount of the organic acid salt of palladium, preferably equimolar thereto.

The coupling reaction should therefore be carried out without a solvent or an additive other than the β-diketone and ethylenediaminetetraacetic acid. The reaction is preferably performed under a partial oxygen pressure of 5 to 200 Kg/cm², most preferably 20 to 100 Kg/cm². When the partial oxygen pressure is lower than 5 Kg/cm², the reaction hardly proceeds. On the other hand, there is no appreciable increase in the yield of the coupling dimer at a partial oxygen pressure above 200 Kg/cm², and therefore, it is not economical to perform the reaction at higher oxygen pressures. Pure oxygen may be used as the oxygen source. However, it is generally safer to use an oxygen-containing gas in which oxygen is diluted with an inert gas such as nitrogen or carbon dioxide gas because of the danger of explosion.

The reaction temperature is generally from 50°C~300°C., preferably from 100° to 200°C., although different temperatures can be used depending on the partial oxygen pressure of the reaction pressure. The reaction time is preferably at least about 30 minutes, usually from about 5 to about 15 hours, and the amount of the dimer produced increases with increasing reaction time (preferably 5~15 hours).

Hydrolysis of the coupling dimer as a mixture of three isomers can be performed by the method heretofore described to give an isomeric mixture of 3,4,3',4'-, 2,3,3',4'- and 2,3,2',3'-isomers. The purification and separation of this isomeric mixture from the reaction product mixture can be performed by methods as are generally employed for such purposes, e.g., distillation, extraction or gas-chromatographic separation. The isomeric mixture, however, can also be easily separated into the constituent isomers by recrystallization based on the difference in solubility of the individual isomers.

Isolation of the constituent isomers from the isomeric mixture of biphenyltetracarboxylic acids can be performed by removing the catalyst by filtration and unreacted matter by distillation from the reaction product mixture after the coupling reaction, directly hydrolyzing it, and thereafter subjecting it to a fractional crystallization. Alternatively, before obtaining biphenyltetracarboxylic acids, that is to say, after isolating the crystals of the dimer consisting of a mixture of the three isomers by distillation and crystallization, the isolated crystals can be hydrolyzed to form the intended biphenyltetracarboxylic acids.

There is no precipitation of palladium in the reaction system during the coupling reaction of dimethyl phthalate. The palladium salt used as the catalyst can be reused after the reaction by purging the autoclave with nitrogen gas and replacing hydrogen gas therein, allowing the autoclave to stand under pressure to reduce the palladium salt in the reaction product mixture, separating the reduced palladium salt as palladium black, filtering and washing it, dissolving it in nitric acid, and adding an organic carboxylic acid such as acetic acid or propionic acid, whereby the catalyst is quantitatively recovered as the organic carboxylic acid salt of palladium (as described in J. Chem. Soc., 3632 (1965) by T. A. Stephenson, S. M. Morehouse, A. R. Powell, J. P. Heffer & G. Wilkinson).

In order to form tetralkyl, e.g., tetramethyl, biphenyls by the coupling reaction of ortho-xylene, the same reaction conditions as are used in the case of dimerizing dimethyl phthalate are employed.

By the oxidative coupling of ortho-xylene under these conditions, 3,4,3',4'-tetramethyl biphenyl (90~60%) is formed as the main product without precipitation of palladium in the reaction system, with 2,3,2',3'(0~3%)-tetramethyl biphenyl and 2,3,3',4'(10~37%)-tetramethyl biphenyl being simultaneously formed. The resulting tetramethyl biphenyls, either as an isomeric mixture of three isomers or after separation into the individual isomers, are oxidized to biphenyltetracarboxylic acids. Preferably, the tetramethyl biphenyls are oxidized with nitric acid or in the presence of an oxidation catalyst.

In the case of oxidation with nitric acid, the tetramethyl biphenyls are heated at 100° to 200°C. for about 2 hours in a 10-20 wt. % aqueous solution of nitric acid, and then heated at a temperature of 200°C~300°C. in a nitric acid solution having concentration of 20~60% by weight, whereby biphenyltetracarboxylic acids corresponding to the above dimers are formed.

When the oxidation is carried out in the presence of an oxidation catalyst, the tetramethyl biphenyl is heated in an atmosphere of oxygen using an aliphatic carboxylic acid such as acetic acid or propionic acid as a solvent to form dimethyldicarboxylic acid-biphenyl. This is then esterified by any generally employed esterification method (Organic Syntheses (1943) 2 264), for example, using an excess of methanol and sulfuric acid to form dimethyl-dimethoxycarbonyl-biphenyl, which is then heated in the presence of the same oxidation catalyst as mentioned above to form dihydroxycarbonyl-dimethoxycarbonylbiphenyl. When this product is hydrolyzed by any generally employed hydrolysis method, for example, using an alkali such as sodium hydroxide or potassium hydroxide, or an acid such as sulfuric acid, a biphenyltetracarboxylic acid corresponding to the above dimer is formed.

When a bromide compound such as ammonium bromide, bromine iodide, manganese bromide, cobalt bromide, hydrogen bromide, or sodium bromide is added to the reaction system during oxidation in the presence of an oxidation catalyst, biphenyltetracarboxylic acid is formed from tetramethyl biphenyl by a one-step oxidation by merely heating the tetramethyl biphenyl in an atmosphere of oxygen in the presence of the oxidation catalyst using an aliphatic carboxylic acid as the solvent.

Examples of the catalyst used are cobalt acetate, manganese acetate, cobalt stearate, cobalt naphthenate, cobalt peracetate, cobalt oleate and cobalt benzoate. A suitable amount of the oxidation catalyst is 1/10 to 1/200, preferably 1/5 to 1/100, parts by weight based on the tetramethyl biphenyl. A suitable amount of the bromide compound is 1/50 to 1/1000, preferably 1/10 to 1/200, parts by weight based on the tetramethyl biphenyl.

Examples of the aliphatic carboxylic acid as a solvent are aliphatic monocarboxylic acids having 2 to 5 carbon atoms, such as formic acid, acetic acid, propionic acid, butyric acid or valeric acid. Of these, acetic acid is especially preferred. The aliphatic carboxylic acid is usually used in an amount of from 1 to 500 times, preferably 2 to 10 times, the weight of the tetramethyl biphenyl.

It is desirable that the oxidation reaction be carried out in an atmosphere of oxygen having a partial pressure of 0.2 to 50 Kg/cm$^2$, preferably 5 to 40 Kg/cm$^2$. A suitable reaction temperature is 50° to 300°C., preferably 80° to 200°C.

According to the present invention, biphenyltetracarboxylic acids which could not obtained by a commercial mass-production process can be easily prepared at high yields from ortho-xylene or dimethyl phthalate, both of which are available at low cost. The biphenyltetracarboxylic acids thus obtained, when converted into their dianhydrides, find a wide range of useful applications, for example as raw materials for the formation of polyimides, epoxy resins, polyesters, curing agents and dyes.

Furthermore, in the present invention, the catalyst used for the oxidative coupling reaction of ortho-xylene or dimethyl phthalate can easily be regenerated as an organic carboxylic acid salt of palladium, and reused, as stated above, with respect to the oxidative coupling of dimethyl phthalate.

The following Examples are given to illustrate the present invention. Unless otherwise indicated in the following Examples all parts and percentages are by weight. Further, unless otherwise indicated, the acids used in the Examples had the following strengths: 98% $H_2SO_4$, 35% HCl and 62% $HNO_3$.

EXAMPLE 1

A one-liter stainless steel autoclave was charged with 0.672 g (3 millimols) of palladium acetate and 300 ml. of ortho-xylene, and a gaseous mixture of nitrogen and oxygen in a molar ratio of 1:1 was introduced therein until the pressure inside the autoclave reached 50 Kg/cm$^2$. With shaking, the ortho-xylene was oxidatively dimerized by heating at 150°C. for 5 hours. No precipitation of palladium was observed in the reaction product mixture.

The autoclave was cooled down to room temperature, and degassed. Nitrogen gas was introduced thereinto, and then the nitrogen replaced by hydrogen gas introduced therein until the interior pressure of the autoclave reached 50 Kg/cm$^2$ (guage). The contents of the autoclave were allowed to stand overnight, and the palladium salt was reduced. The autoclave was degassed, and the precipitated palladium black (0.31 g) was filtered.

The filtrate was distilled at a reduced pressure of 20 mm Hg to evaporate off unreacted ortho-xylene. Further distillation at 4 mm Hg gave 32.8 g of a fraction boiling at 148 to 167°C/4 mm Hg. Gas-chromatographic analysis of this fraction showed that it consisted of 1% by weight of 2,3,2',3'-tetramethyl biphenyl, 25% by weight of 2,3,3',4'-tetramethyl biphenyl and 74% by weight of 3,4,3',4'-tetramethyl biphenyl. It was confirmed that the yield of this fraction was 5200 mol % based on palladium acetate.

EXAMPLES 2 TO 7

In each run, a one-liter stainless steel autoclave was charged with 300 ml. of ortho-xylene, the organic acid salt shown in Table 1 as the catalyst and the additive shown in Table 1, and a gaseous mixture of nitrogen and oxygen at a molar ratio of 1:1 was introduced therein until the pressure inside the autoclave reached 50 Kg/cm$^2$. With stirring, the ortho-xylene was oxidatively dimerized at 150°C. for 8 hours. The dimerized product was cooled, and as in Example 1 the catalyst was separated by filtration as palladium black. Distillation of the filtrate under reduced pressure gave a fraction having a boiling point of 148°-167°C./4 mm Hg. Gas-chromatographic analysis of this fraction showed that it consisted of 2,3,2',3'-, 2,3,3',4'- and 3,4,3',4'-tetramethyl biphenyls in the total amount shown in Table 1.

This fraction was placed in an autoclave lined with titanium, and the aliphatic carboxylic acid, oxidation catalyst and bromide compound shown in Table 1 were added. Air at a pressure of 40 Kg/cm$^2$ was passed into the autoclave at a rate of 50 liters/hr., and the fraction was reacted at 200°C. for 4 hours. The contents of the autoclave were cooled and filtered. The precipitate obtained was washed with water and recrystallized from methanol to yield an isomeric mixture of 2,3,2',3'-, 2,3,3',4'- and 3,4,3',4'-biphenyl tetracarboxylic acids in the amount shown in Table 1.

Table 1

| Examples | 2 | 3 | 4 | 5 | 6 | 7 |
|---|---|---|---|---|---|---|
| Organic acid salt of palladium (m-mols) | A-1 2 | A-1 2 | A-1 2 | A-2 2 | A-3 2 | A-4 2 |
| Additive (m-mols) | B-1 2 | B-2 2 | none | B-3 2 | none | B-1 2 |
| Yield of tetramethyl biphenyls (g) and yield (%) (mol% based on palladium salt) | 22.7 5400 | 17.7 4200 | 13.0 3100 | 15.3 3600 | 17.3 4100 | 21.1 5000 |
| Aliphatic carboxylic acid (milliliters) | C-1 80 | C-2 80 | C-1 80 | C-1 80 | C-1 80 | C-2 80 |
| Oxidation catalyst (m-mols) | D-3 1.5 | D-2 1.5 | D-2 1.5 | D-1 1.5 | D-3 1.5 | D-1 1.5 |
| Bromide (m-mols) | E-1 3.0 | E-2 3.0 | E-1 3.0 | E-2 3.0 | E-3 3.0 | E-1 3.0 |
| Amount yielded of isomeric mixture of biphenyltetracarboxylic acids (g) | 20.3 | 13.9 | 11.6 | 11.3 | 16.3 | 19.5 |

The symbols used in Table 1 have the following meanings.
A-1: palladium acetate;
A-2: palladium propionate;
A-3: acetylacetonate palladium (II);
A-4: bis(dibenzalacetone) palladium (O)
B-1: acetylacetone;
B-2: ethylenediaminetetraacetic acid;
B-3: trifluoroacetylacetone
C-1: acetic acid;
C-2: propionic acid
D-1: cobalt stearate;
D-2: cobalt naphthenate;
D-3: cobalt acetate
E-1: ammonium bromide;
E-2: sodium bromide;
E-3: hydrogen bromide

EXAMPLE 8

A 5-liter electromagnetically stirred stainless steel autoclave was charged with 2.5 liters (2980 g) of dimethyl phthalate and 3.36 g (0.015 mol) of palladium acetate, and a gaseous mixture of nitrogen and oxygen at a molar ratio of 1:1 was introduced therein until the pressure inside the autoclave reached 50 Kg/cm$^2$. The reaction of dimethyl phthalate was performed while the relationship between the reaction time and the amount of the dimer yielded was being measured by occasionally extracting small samples. When the interior of the autoclave was maintained 130°–134°C. for one hour and then reaction of dimethyl phthalate was carried out at 150°C. for one hour, the amount of the resulting dimer was 3060 mol % (based on the palladium acetate). When the reaction was carried out for 7 hours at 150°C., the amount of the dimer obtained was 5650 mol %, and when the reaction was further carried out at 150°C for a total of 12 hours, the amout of the dimer reached 7800 mol %. Analysis was conducted using gas-chromatography, and a total of 225 g of the sample was extracted for measurement purposes.

After reaction for a total of 12 hours at the conditions described, the autoclave was cooled to room temperature. Oxygen gas was removed from the system, and hydrogen gas was introduced into the autoclave until the pressure inside the autoclave reached 50 Kg/cm$^2$. The contents were heated at 60°C. for one hour, and allowed to stand overnight. Then, the reaction product mixture was filtered, and 1.5 g of palladium black precipitated by hydrogen reduction was recovered and removed.

The resulting reaction product mixture (2755 g) was distilled under reduced pressure (3 mm Hg) over a hot oil bath, and 40 g of water formed and 2110 g of unreacted dimethyl phthalate removed. Methanol (1 liter) was added to the distillate and, on standing overnight, crystals precipitated. The crystals were filtered, and washed with methanol to yield crude crystals (1) (tetramethyl biphenyl-2,3,3',4'-tetracarboxylate having a purity of more than 98%).

Methanol was evaporated off from the methanol residue, and the residue was distilled under reduced pressure over a salt bath to give 303 g of a fraction (2) having a boiling point of 250° to 300°C./1 mm Hg.

The fraction (2) was dissolved in 200 ml. of methanol, decolorized with activated carbon, and cooled to yield 217 g of white crystals. Analysis of the white crystals by gas-chromatography showed that they were a composition consisting of 1% tetramethyl biphenyl-2,3,2',3'-tetracarboxylate, 50% tetramethyl biphenyl-2,3,3',4'-tetracarboxylate, 49% tetramethyl biphenyl-3,4,3',4'-tetracarboxylate, and traces of unidentifiable substances. 100 g of the white crystals were taken out, and 250 ml. of water, 250 ml. of acetic acid and 50 ml. of (98%) sulfuric acid were added thereto. The mixture was heated under reflux over an oil bath at 140°C. for 8 hours, and cooled to precipitate crystals. Filtration of these crystals yielded 44 g of white crystals.

When these crystals were recrystallized from acetone, white crystals of biphenyl-3,4,3',4'-tetracarboxylic acid having a purity of more than 99% were obtained. when the filtrate obtained after filtration of said white crystals (44 g) was concentrated under reduced pressure, 40 g of white crystals were obtained. Recrystallization of these white crystals from water yielded white crystals of biphenyl-2,3,3',4'-tetracarboxylic acid having a purity of more than 90%.

EXAMPLES 9 TO 16

In each run, a 1-liter stainless steel autoclave was charged with 300 ml. of dimethyl phthalate and the organic acid salt of palladium shown in Table 2 with or without the further addition of the additive shown in Table 2, and a gaseous mixture of nitrogen and oxygen at a molar ratio of 1:1 was introduced thereinto until the pressure inside the autoclave reached 50 Kg/cm$^2$. With stirring, the coupling reaction of dimethyl phthalate was performed at 150°C. for 23 hours to yield a dimer consisting of three isomers of tetramethyl biphenyltetracarboxylate in the yield shown in Table 2.

The isomeric mixture obtained was hydrolyzed in the same way as in Example 8 to yield a mixture of 2,3,2',-

3'-, 2,3,3',4'- and 3,4,3',4'-biphenyltetracarboxylic acids.

The identification and quantitative determination of the dimers were carried out by gas-chromatography. The biphenyltetracarboxylic acids were analyzed using gas-chromatography after converting them to their tetramethyl esters, and the values obtained were converted on the basis of the biphenyltetracarboxylic acids. The yields are expressed in mol percent based on the palladium salt used. Conversion was accomplished by forming a mixture of ester (1 part by weight), 98% $H_2SO_4$ (1 part by weight) and $CH_3OH$, (10 parts by weight) and then refluxing for 4 hours.

Table 2

| Examples | Palladium salt (millimols) | Additive (millimols) | Yield of dimer (mol %) | Yield of biphenyltetracarboxylic acid (mol %) |
| --- | --- | --- | --- | --- |
| 9 | Palladium acetate (2) | Acetylacetone (2) | 9000 | 8600 |
| 10 | Ditto | none | 1800 | 1600 |
| 11 | Ditto | Ethylenediaminetetraacetic acid (2) | 5000 | 3900 |
| 12 | Ditto | Benzoylacetone (2) | 6100 | 4700 |
| 13 | Palladium propionate (2) | none | 1600 | 1200 |
| 14 | Palladium benzoate (2) | none | 1700 | 1200 |
| 15 | Ditto | Acetylacetone (2) | 7400 | 6600 |
| 16 | Dibenzylidene acetone palladium (II) | none | 3300 | 2600 |

EXAMPLES 17 TO 19

Biphenyltetracarboxylic acids were prepared under the same conditions as in Example 8 except that the pressure inside the autoclave was changed as shown in Table 3. The results obtained are shown in Table 3. The yield of biphenyl tetracarboxylic acid was expressed in mol percent based on the palladium acetate used.

Table 3

| Examples | 17 | 18 | 19 |
| --- | --- | --- | --- |
| Pressure inside the autoclave (Kg/cm²) | 40 | 80 | 100 |
| Yields of biphenyl tetracarboxylic acids (mol%) | 4900 | 9700 | 9700 |

EXAMPLE 20

A 1-liter shaking-type autoclave was charged with 300 ml. of dimethyl ortho-phthalate, 0.448 g of palladium acetate and 0.20 g of acetylacetone, and a gaseous mixture of nitrogen and oxygen at a molar ratio of 1:1 was introduced thereinto until the pressure inside the autoclave reached 50 Kg/cm². The coupling reaction of dimethyl ortho-phthalate was performed at 150°C. for 23 hours. After the reaction, the inside of the autoclave was degassed, and hydrogen gas was introduced thereinto until the pressure inside the autoclave reached 50 Kg/cm², followed by standing overnight.

The contents were withdrawn, and the palladium black precipitated (0.202 g) was filtered. The filtrate was concentrated by distillation at 250°C. and 3 mm Hg on an oil bath, and unreacted dimethyl ortho-phthalate was recovered. The filtrate then was further distilled at 250°–350°C. at 1 mm Hg over a salt bath to yield 62.6 g of a fraction having a boiling point of 250°–350°C./1 mm Hg. The 2,3,2',3'-isomer was contained in a fraction of the residue, i.e., a fraction having a boiling point below 250°C/1 mm Hg.

To 62.6 g of this fraction was added a small amount of activated carbon, followed by dissolution in 100 ml. of methanol. The solution was filtered and cooled to form 43 g of white crystals. Gas-chromatographic analysis of these white crystals showed that they consisted of tetramethyl 2,3,3',4'- and 3,4,3',4'-biphenyltetracarboxylates. The molar ratio of the 2,3,3',4'-isomer to the 3,4,3',4'-isomer was 75:25.

43 g of the resulting isomeric mixture of tetramethyl biphenyltetracarboxylates as white crystals were admixed with 100 ml. of water, 100 ml. of acetic acid and 20 ml. of 98% sulfuric acid, and hydrolyzed by heating under reflux for 4 hours. Upon cooling, crystals were precipitated.

These crystals were filtered and washed with water to form 7.7 g of white crystals having a melting point of 302 to 306°C., which were identified as 3,4,3',4'-biphenyltetracarboxylic acid, the filtrate containing the 2,3,3',4'-isomer.

EXAMPLE 21

To 150 g of an isomeric mixture of tetramethyl biphenyltetracarboxylates (molar ratio of 2,3,2',3'-: 2,3,3',4'-: 3,4,3',4'-being 1 : 56 : 43) were added 250 ml. of water, 250 ml. of acetic acid and 70 ml. of 35% hydrochloric acid. The isomeric mixture was hydrolyzed by heating under reflux for 10 hours. The reaction product mixture was cooled with ice, and the white crystals precipitated were filtered to yield 69.9 g of white crystals of 3,4,3',4'-biphenyltetracarboxylic acid. Concentration of the filtrate yielded 39.3 g of white crystals of 2,3,3',4'-biphenyltetracarboxylic acid. The filtrate contained the 2,3,2',3'- and 2,3,3',4'-isomers.

EXAMPLE 22

To 50.3 g of an isomeric mixture of tetramethyl biphenyltetracarboxylate (the molar ratio of 2,3,3',4'-: 3,4,3',4'-being 54 : 46) were added 40 g of potassium hydroxide, 400 ml. of methanol and 100 ml. of water. The isomeric mixture was hydrolyzed by heating under reflux for 7 hours.

35% hydrochloric acid was added to the filtrate until the pH was below 1, followed by cooling with ice. The crystals separated were filtered, washed with water, and dried to provide 19.3 g of 3,4,3',4'-biphenyltetracarboxylic acid crystals having a melting point of 295° to 302°C.

Recovery of the 2,3,3',4'-isomer from the filtrate was difficult because sodium chloride was comingled therewith as an impurity.

EXAMPLE 23

To 73.0 g of an isomeric mixture of tetramethyl 2,3,3',4'- and 3,4,3',4'-biphenyltetracarboxylates (48% of the 2,3,3',4'-isomer and 52% of the 3,4,3',4'-isomer) were added 100 ml. of 35% hydrochloric acid and 100 ml. of acetic acid, and the mixture was heated under reflux for 5 hours. The reaction product mixture was concentrated by distillation at reduced pressure, and on further addition of 100 ml. of concentrated hydrochloric acid, heated under reflux for 5 hours to thereby convert the above isomeric mixture to an isomeric mixture of biphenyltetracarboxylic acids.

The isomeric mixture of biphenyltetracarboxylic acids was evaporated to dryness, and with the addition of 300 ml. of acetic anhydride, heated under reflux for 5 hours to convert it to an isomeric mixture of biphenyltetracarboxylic dianhydrides. Acetic acid formed was distilled off at reduced pressure, and the mixture was concentrated by distillation so that its amount was reduced to about half its original value. The crystals separated in the mixture were quickly separated by hot filtration.

These crystals were identified as 3,4,3',4'-biphenyltetracarboxylic dianhydride, and the amount yielded was 25.6 g (89% of theoretical).

When the filtrate resulting after the separation of 3,4,3',4'-biphenyltetracarboxylic dianhydride was cooled to 5°C., white crystals precipitated. These white crystals were separated by filtration to form 16.6 g of a substance having a melting point of 188° to 195°C. The filtrate was concentrated by distillation and cooled to yield 5.4 g of white crystals having a melting point of 185° to 194°C. These crystals (16.6 g and 5.4 g) were both 2,3,3',4'-biphenyltetracraboxylic dianhydride. The yield was 82% of theoretical the identification of the 2,3,3',4'-biphenyltetracarboxylic dianhydride was performed by melting point and infrared absorption spectroscopy.

The 2,3,3',4'- and 3,4,3',4'-biphenyltetracarboxylic dianhydrides both had a purity of more than 96%. By further repeating recrystallization using acetic anhydride, purity can be increased to more than 99%.

The purity of the biphenyltetracarboxylic dianhydride was determined by gas-chromatographic analysis of its ester formed by heating it with methanol and sulfuric acid. A purity of 96% means the presence of 4% of isomers.

EXAMPLE 24

An isomeric mixture of biphenyltetracarboxylic acids obtained as in Example 23 was treated as in Example 23 except that 400 ml. of propionic anhydride was used instead of 300 ml. of acetic anhydride for conversion to an isomeric mixture of biphenyltetracarboxylic dianhydrides. There were obtained 26.4 g (91% of theoretical) of 3,4,3',4'-biphenyltetracarboxylic dianhydride having a melting point of 295° to 302°C. and 21.2 g (79% of theoretical) of 2,3,3',4'-biphenyltetracarboxylic dianhydride having a melting point of 195° to 200°C., both at a purity of more than 96%.

EXAMPLE 25

Acetic anhydride (150 ml.) was added to 54.3 g of an isomeric mixture of 51% of 2,3,3',4'-biphenyltetracarboxylic acid and 49% of 3,4,3',4'-biphenyltetracarboxylic acid, and the mixture was heated under reflux for 10 hours. By distillation under reduced pressure, about 50 ml. of a liquid (a mixture of acetic acid and acetic anhydride) was evaporated off. With the addition of 100 ml. of acetic anhydride, the mixture was further heated for 5 hours to form an isomeric mixture of biphenyltetracarboxylic dianhydrides. The crystals precipitated in the reaction product mixture were hot filtered to provide 19.0 g (80% of theoretical) of 3,4,3',4'-biphenyltetracarboxylic dianhydride having a melting point of 295° to 305°C.

The filtrate was treated in the same way as in Example 23 to provide 3.9 g of crystals having a melting point of 180° to 201°C. and 17.1 g of crystals having a melting point of 195° to 200°C., both which were 2,3,3',4'-biphenyltetracarboxylic dianhydride having a purity of more than 96%. The yield was 88% of theoretical.

EXAMPLE 26

The procedure of Example 25 was repeated except that 350 ml. of propionic anhydride were used instead of acetic anhydride (150 ml. + 100 ml.). There were obtained 21.0 g (88% of theoretical) of 3,4,3',4'-biphenyltetracarboxylic dianhydride having a melting point of 295° to 302°C. and 18.0 g (76% of theoretical) of 2,3,3',4'-biphenyltetracarboxylic dianhydride having a melting point of 195° to 200°C., both having a purity of more than 98%.

EXAMPLE 27

Acetone (100 ml.) was added to 20.0 g of 2,3,3',4'-biphenyltetracarboxylic dianhydride and 3,4,3',4'-biphenyltetracarboxylic dianhydride present at a 50%–50% isomeric mixture, and the mixture was heated under reflux for 30 minutes. A solid insoluble in the acetone was quickly separated by hot filtration to provide 11.2 g of a white solid.

To this solid (11.2 g) was added 50 ml. of acetone, and the mixture was heated with stirring. Subsequent hot filtration provided 8.5 g of white crystals having a melting point of 295° to 300°C. which were identified as 3,4,3',4'-biphenyltetracarboxylic dianhydride. The yield was 80.5% (of theoretical). To 8.5 g of this 3,4,3',4'-biphenyltetracarboxylic dianhydride were added 100 ml. of methanol and 5 ml. of 98% of sulfuric acid, and the mixture was heated under reflux for 10 hours. Gas-chromatographic analysis of the resulting reaction mixture showed that esterification was complete and the purity of the product was 98.6%, with the presence of 1.4% of the 2,3,3',4'-isomer.

On the other hand, when the filtrate resulting after the filtration of 11.2 g of the white solid was evaporated to dryness, 7.8 g (yield 78%) of 2,3,3',4'-biphenyltetracarboxylic dianhydride having a melting point of 192° to 202°C. was obtained. Gas-chromatographic analysis of this product after conversion to its ester in the same manner as above showed that its purity was 92.6%, with the presence of 7.4% of the 2,3,3',4'-isomer.

EXAMPLE 28

Acetic anhydride (400 ml.) was added to 116 g of 2,3,3',4'-biphenyltetracarboxylic acid having a melting point of 195° to 205°C., and the mixture was heated under reflux for 4 hours. The mixture was cooled, and allowed to stand. The crystals formed were filtered to provide 83 g (yield 80% of theoretical) of 2,3,3',4'-biphenyltetracarboxylic dianhydride having a melting point of 196° to 204°C. By further concentration of the filtrate, 17 g (16%) of 2,3,3',4'-biphenyltetracarboxylic dianhydride was obtained.

The analytical values of this 2,3,3',4'-biphenyltetracarboxylic dianhydride as a novel substance were as follows:
1. Elemental analysis values
   Found: C, 65.08; H, 2.07
   Calculated: C, 65.31; H, 2.07 (for $C_{16}H_6O_6$)
2. Infrared spectrum
   Intensity of absorption (s: strong, m: medium, w: weak)
   3100 cm$^{-1}$ w, 1940 s, 1770 s, 1600 s, 1460 w, 1340 m, 1260 s, 1210 m, 1180 m, 1150 m, 920 s, 860 w, 850 w, 820 w, 750 s, 700 w, 690 w, 650 w, 580 w, 540 w.
3. Nuclear magnetic resonance spectrum (in $CDCl_3$)
   3.70 (s, 3; 2-COOCH$_3$), 3.91 (s, 9; 3,3',4'-COOCH$_3$), 7.50–7.55 (m, 3; 5,6,6'-H), 7.72 (s, 1; 2'-H), 7.75–7.85 (d, 1; 5'-H), 7.96–8.12 (t, 1; 4-H).

In the nuclear magnetic resonance spectrum, the sample was prepared by adding methanol and sulfuric acid, to 2,3,3',4'-biphenyltetracarboxylic acid, heating the mixture under reflux, driving off methanol, neutralize the product with sodium carbonate, extracting it with benzene, and recrystallizing the product with methanol to form tetramethyl 2,3,3',4'-biphenyltetracarboxylate.

Figures 4A, 4B:
FIG. 4A shows the n m r spectra of tetramethyl 2,3,3',4'-biphenyltetracarboxylate in $CDCl_3$, and 4B is an enlarged view of, 4A indicated the portion of Figure by $a$.

The infrared spectrum is shown in FIG. 3, and the nuclear magnetic resonance spectrum in FIG. 4.

EXAMPLE 29

Acetic anhydride (250 ml.) was added to 75 g of 3,4,3',4'-biphenyltetracarboxylic acid having a melting point of 295° to 305°C., and the mixture was heated under reflux for 5 hours, followed by cooling with ice. The precipitate was filtered to provide 52 g (yield 78% of theoretical) of 3,4,3',4'-biphenyltetracarboxylic dianhydride having a melting point of 295° to 308°C. Further concentration of the filtrate gave 2 g (3% of theoretical) of 3,4,3',4'-biphenyltetracarboxylic dianhydride.

While the invention has been described in detail and with reference to specific embodiments thereof, it will be apparent to one skilled in the art that various changes and modifications can be made therein without departing from the spirit and scope thereof.

What we claim is:

1. A process for separating biphenyltetracarboxylic dianhydride isomers from a mixture of these isomers, which comprises fractionally crystallizing said mixture in a solvent selected from the group consisting of saturated aliphatic acid anhydrides and ketones while heating to a temperature of from about 50°C to about 250°C to thereby separate the mixture into its constituent isomers.

2. The process of claim 1 wherein said aliphatic acid anhydride is a member selected from the group consisting of acetic anhydride, propionic anhydride and butyric anhydride and caproic anhydride, and said ketone is a member selected from the group consisting of acetone diethylketone, diisopropylketone and dibutylketone.

3. The process of claim 1 wherein said biphenyltetracarboxylic dianhydride isomers comprise the 2,3,2',3'-isomer, the 2,3,3',4'-isomer and 3,4,3',4'-isomer, present in amounts of 0 to 3%, 10 to 80% and 90 to 17%, respectively, all percents being by weight.

* * * * *